United States Patent
Wilson

(10) Patent No.: US 10,966,678 B2
(45) Date of Patent: *Apr. 6, 2021

(54) BONE DENSITOMETER

(71) Applicant: Hologic, Inc., Marlborough, MA (US)

(72) Inventor: Kevin Wilson, Acton, MA (US)

(73) Assignee: Hologic, Inc., Marlborough, MA (US)

( * ) Notice: Subject to any disclaimer, the term of this patent is extended or adjusted under 35 U.S.C. 154(b) by 15 days.

This patent is subject to a terminal disclaimer.

(21) Appl. No.: 16/549,184

(22) Filed: Aug. 23, 2019

(65) Prior Publication Data

US 2020/0046307 A1 Feb. 13, 2020

Related U.S. Application Data

(63) Continuation of application No. 15/589,080, filed on May 8, 2017, now Pat. No. 10,390,784, which is a continuation of application No. 14/553,533, filed on Nov. 25, 2014, now Pat. No. 9,642,585.

(60) Provisional application No. 61/908,329, filed on Nov. 25, 2013.

(51) Int. Cl.
*A61B 6/00* (2006.01)

(52) U.S. Cl.
CPC .......... *A61B 6/5211* (2013.01); *A61B 6/4452* (2013.01); *A61B 6/505* (2013.01)

(58) Field of Classification Search
CPC ........ G01N 23/00; G01N 23/02; G01N 23/04; G01N 23/06; G01N 23/063; G01N 23/08; G01N 23/083; G01N 23/087; A61B 6/00; A61B 6/505; A61B 6/4452; A61B 6/5211; G06T 7/0012; G06T 7/0014; G06T 7/0024; G06T 7/0028; H05G 1/64

See application file for complete search history.

(56) References Cited

U.S. PATENT DOCUMENTS

| | | |
|---|---|---|
| 4,831,527 A | 5/1989 | Clark |
| 5,305,368 A | 4/1994 | Bisek et al. |
| 6,081,582 A | 6/2000 | Mazess et al. |
| 6,160,866 A | 12/2000 | Mazess |
| 6,173,034 B1 | 1/2001 | Chao |
| 7,725,153 B2 | 5/2010 | Kelly et al. |
| 8,300,911 B1 | 10/2012 | Payne et al. |
| 8,792,689 B2 | 7/2014 | Kelly et al. |
| 9,179,873 B2 | 11/2015 | Kelly et al. |
| 9,642,585 B2 | 5/2017 | Wilson |
| 10,390,784 B2 | 8/2019 | Wilson |
| 10,499,865 B2 | 12/2019 | Wilson et al. |
| 2002/0070365 A1 | 6/2002 | Karellas |

(Continued)

FOREIGN PATENT DOCUMENTS

WO 2014/066906 5/2014

OTHER PUBLICATIONS

Lehmann et al., "Generalized Image Combinations in Dual KVP Digital Radiography", Med. Phys. 8(5) Sep./Oct. 1981, 9 pgs.

(Continued)

*Primary Examiner* — Jurie Yun

(74) *Attorney, Agent, or Firm* — Merchant & Gould P.C.

(57) ABSTRACT

A method includes moving a radiation source and a radiation detector along a scan path substantially transverse to a longitudinal axis of a patient. A beam of radiation is emitted from the radiation source. The beam of radiation is detected at the radiation detector. The detected beam is processed so as to form a first image of a first area of the patient along the scan path.

21 Claims, 6 Drawing Sheets

(56) References Cited

U.S. PATENT DOCUMENTS

| | | |
|---|---|---|
| 2006/0074288 A1 | 4/2006 | Kelly et al. |
| 2007/0238957 A1 | 10/2007 | Yared |
| 2010/0234719 A1 | 9/2010 | Kelly et al. |
| 2011/0235886 A1 | 9/2011 | Kelly et al. |
| 2014/0288420 A1 | 9/2014 | Goossen et al. |
| 2014/0371570 A1 | 12/2014 | Davis et al. |
| 2015/0146851 A1 | 5/2015 | Wilson |
| 2017/0046837 A1 | 2/2017 | Leinhard et al. |
| 2018/0049710 A1 | 2/2018 | Wilson |
| 2020/0029927 A1 | 1/2020 | Wilson |
| 2020/0060636 A1 | 2/2020 | Wilson |

OTHER PUBLICATIONS

WHO publication—Kanis JA, on behalf of the World Health Organisation Scientific Group, "Assessment of osteoporosis at the primary health care level", WHO Collaborating Centre for Metabolic Bone Diseases, University of Sheffield 2007, 339 pgs.

Shane, E., et al. "Atypical subtrochanteric and diaphyseal femoral fractures: report of a task force of the American Society for Bone and Mineral Research." J Bone Miner Res. Nov. 2010;25(11):2267-94.

Shane, E., et al."Atypical subtrochanteric and diaphyseal femoral fractures: Second report of a task force of the American society for bone and mineral research." J Bone Miner Res. May 28, 2013. doi: 10.1002/jbmr.1998. [Epub ahead of print], pp. 1-23.

McKieman F.E., et al. "A long femur scan field does not alter proximal femur bone mineral density measurements by dual-energy X-ray absorptiometry." J Clin Densitom. Jul.-Sep. 2011;14(3):354-8.

De Lorenzo, A. et al., "Predicting body cell mass with bioimpedance by using theoretical methods: a technological review", J. Appl. Physiol 1997; 82: 1542-58.

Lustgarten, M.S. et al., "Assessment of Analytical Methods Used to Measure Changes in Body Composition in the Elderly and Recommendations for Their Use in Phase II Clinical Trials", J. Nutr, Heath Aging, 15(5): 368-375 (2011).

Malkov, S. et al., "Combining 3D optical imaging and dual energy absorptiometry to measure three compositional components", Progress in Biomedical Optics and Imaging, SPIE—Int'l. Society for Optical Engineering, 8937: 893714-893714-6 (2014).

PCT International Preliminary Report on Patentability in International Application PCT/US2016/019562, dated Aug. 29, 2017, 8 pgs.

PCT International Search Report and Written Opinion in International Application PCT/US2018/023817, dated Sep. 4, 2018, 15 pages.

PCT International Search Report and Written Opinion in International Application PCT/US2016/019562, dated Jul. 21, 2016, 15 pages.

Pietrobelli, A. et al., "Dual-energy X-ray absorptiometry: fat estimation errors due to variation in soft tissue hydration", The American Physiological Society, E808-E816 (1998).

Prado, C. et al., "Lean Tissue Imaging: A New Era for Nutritional Assessment and Intervention", Journal of Parental and Enteral Nutrition, 38(8): 940-953 (2014).

Sayer, A.A. et al., "New horizons in the pathogenesis, diagnosis and management of sarcopenia", Age and Ageing, 42: 145-150 (2013).

Sorenson, J.A. et al., "Simulation of dual-energy x-ray absorptiometry", Medical Physics, 16(1): 75-80 (1989).

Wear, J. et al., "CZT detector for dual-energy x-ray absorptiometry (DEXA)", Proceedings of SPIE, 4142: 175-188 (2000).

Wilson, J.P. et al., "Improved 4-Compartment body-composition model for a clinically accessible measure of total body protein", Am J Clin Nutr. 2013; 97: 497-504.

Wilson, J.P. et al., "Dual-Energy X-Ray absorpitometry-based body volume measurement for 4-compartment body composition", The American Journal of Clinical Nutrition, 2012; 95 (1): 25-31.

PCT International Preliminary Report and on Patentability in International Application PCT/US2018/023817, dated Oct. 1, 2019, 7 pages.

Michael et al., "Monte Carlo modelling of an extended DXA technique", Physics in Medicine and Biology, vol. 43, No. 9, Sep. 1, 1998, pp. 2583-2596.

European Communication in Application 18716810.9, dated Nov. 10, 2020, 9 pages.

BONE DENSITOMETER

CROSS-REFERENCE TO RELATED APPLICATIONS

This application is a continuation of U.S. patent application Ser. No. 15/589,080 (now U.S. Pat. No. 10,390,784), filed May 8, 2017, which application is a continuation of U.S. patent application Ser. No. 14/553,533 (now U.S. Pat. No. 9,642,585), filed Nov. 25, 2014, which application claims priority to and the benefit of U.S. Provisional Application Ser. No. 61/908,329, filed Nov. 25, 2013, entitled "Bone Densitometer," the disclosures of which are hereby incorporated by reference herein in their entirety.

BACKGROUND

Scanning radiographic equipment differs from conventional radiography in that it employs a narrowly collimated beam of radiation, typically x-rays, formed into, for example, a fan beam, rather than a broad area cone beam. The compact beam size allows the replacement of an image forming sheet of radiographic film, used with conventional radiographic equipment, with a small area array of electronic detector elements. Further, the scanning allows the collection of data over a much broader area than would be practical with a single x-ray cone beam.

The electronic detector elements receiving the transmitted radiation produce electrical signals which may be converted to digital values by an analog-to-digital converter for the later development of an image or for other processing by computer equipment. The ability to quantify the measurement of the transmitted radiation, implicit in the digitization by the analog to digital converter, allows not only the formation of a radiographic "attenuation" image but also the mathematical analysis of the composition of the attenuating material by dual energy techniques. Such dual energy techniques quantitatively compare the attenuation of radiation at two energies to distinguish, for example, between bone and soft tissue. This makes possible the measurement of bone mass, such measurement being important in the treatment of osteoporosis and other bone diseases.

Bone densitometers, particularly central dual-energy absorptiometers (central DXA or DEXA), are used to measure the proximal femur for bone mineral content (BMC) and bone mineral area density ($g/cm^2$) (commonly referred to as bone mineral density or BMD). The BMD of the proximal femur is used to diagnose osteoporosis and predict future hip and other osteoporotic fracture risk. When performing a central DXA scan to measure the BMD of the proximal hip, only a couple of centimeters below the lessor trochanter to a couple of centimeters above the head of the femur is typically imaged.

Reduction of fracture risk is commonly accomplished by anti-resorptive medications, one class of which is bisphonates (e.g., alendronate sodium, risedronate sodium, ibandronate sodium, zoledronic acid, etc.). It has been determined, that bisphophonates, and likely other anti-resorptives used to reduce fracture risk in primary and secondary osteoporosis, are associated with atypical femoral fractures (AFFs). Atypical femoral fractures seem to be stress fractures that develop over a period of time, in some cases, months to years. AFFs occur below the lessor trochanter and above the supracondylar flare and are often bilateral. Developing AFFs are associated with focal thickening of the lateral cortex due to local endosteal and periosteal reactions. Additionally, as AFFs progress, they may be associated with a transverse radiolucent line. Developing AFFs can be seen with a number of different radiologic modalities, including central DXA, x-ray radiographs, magnetic resonance imaging (MRI), computed tomography (CT) scans, and bone scans. While developing AFFs may be seen on DXA, a typical clinical DXA exam encompasses only a small fraction of the region where AFFs occur. While the DXA region when performing proximal femur BMD measurements can be extended, typically only one half of the average adult femur can be imaged. It is also possible to detect signs that are associated with AFFs by using a separate, single-energy, high resolution scan capable of imaging the entire femur for visualization of traits associated with an incomplete or developing AFF.

Regarding the form of the radiation used in bone DXA systems, the compact beam of radiation used in scanning radiographic systems allows the use of limited area detectors permitting high resolution with relatively lower cost. Further, the images formed by a compact beam are potentially more accurate than those produced by a typical broad beam radiographic system. The accuracy arises from the limited divergence of the rays of the beam as compared to a broad area cone beam. This narrow collimation of the fan beam reduces "parallax" in the projected image, particularly of anatomical planar surfaces that are nearly parallel with the central ray of the beam.

The compact beam of radiation, however, also requires increased scanning motion if large areas are to be measured. In a fan beam system, typically the fan beam will be scanned in a raster or "zig-zag" pattern over the area to be measured, each line of the scan forming a scan image separated by somewhat less than the width of the fan beam to ensure complete illumination of the entire volume of the imaged object. The direction of scanning is generally perpendicular to the direction of the radiation and the plane of the fan beam. In general, each scan path is generally parallel to a longitudinal axis of a patient being scanned.

SUMMARY

In one aspect, the technology relates to a method which includes moving a radiation source and a radiation detector along a scan path substantially transverse to a longitudinal axis of a patient; emitting a beam of radiation from the radiation source; detecting the beam of radiation at the radiation detector; and processing the detected beam so as to form a first image of a first area of the patient along the scan path. In an embodiment, the method further includes processing the detected beam so as to form a second image of a second area of the patient along the scan path, wherein the second area of the patient is adjacent to the first area. In another embodiment, the scan path encompasses a plurality of adjacent areas of the patient disposed along the scan path. In another embodiment, the method further includes determining a degree of image alignment between adjacent portions of the first image and the second image. In yet another embodiment, the method further includes adjusting adjacent portions of the first image and the second image based at least in part on the degree of image alignment. In still another embodiment, the method further includes merging the first image and the second image at the adjusted adjacent portions to form a composite image.

In another embodiment of the above aspect, the method further includes displaying the composite image. In an embodiment, determining the degree of image alignment includes analyzing only a selected structure of the patient. In another embodiment, the selected structure includes a bone.

In yet another embodiment, determining the degree of image alignment includes determining a height of the selected structure. In still another embodiment, the method further includes scaling at least one of the first image and the second image based at least in part on the height of the selected structure.

In another aspect, the technology relates to a method which includes: emitting a beam of radiation along a first scan path, wherein the first scan path is substantially transverse to a longitudinal axis of a patient; detecting the beam of radiation along the first scan path; processing the detected beam so as to form a plurality of first scan path images of the patient; and determining a degree of image alignment between adjacent portions of adjacent images of the plurality of first scan path images. In an embodiment, the method further includes merging the adjacent images of the first scan path images at the adjacent portions to form a first scan path composite image. In another embodiment, the method further includes: emitting a beam of radiation along a second scan path, wherein the second scan path is substantially transverse to a longitudinal axis of a patient and substantially parallel to the first scan path; detecting the beam of radiation along the second scan path; processing the detected beam so as to form a plurality of second scan path images of the patient; determining a degree of image alignment between adjacent portions of adjacent images of the plurality of second scan path images; and determining a degree of image alignment between adjacent portions of adjacent images of the plurality of second scan path images and the plurality of first scan path images. In yet another embodiment, the method further includes merging the adjacent images of the second scan path images at the adjacent portions to form a second scan path composite image. In still another embodiment, the method further includes merging the adjacent images of the second scan path images and the first scan path images at adjacent portions to form a master composite image.

In another aspect, the technology relates to determining the degree of image alignment including analyzing only a selected structure of the patient. In an embodiment, the selected structure includes a bone. In another embodiment, determining the degree of image alignment includes determining a height of the selected structure. In yet another embodiment, the method further includes scaling at least one of a plurality of adjacent first scan path images based at least in part on the height of the selected structure.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The present technology provides a system and methods suitable for transverse scanning of at least a portion of a patient that optimizes assessment of AFFs of both the right and left femurs using an extremely compact fan beam transverse across both legs of a patient in a single scan. The technologies described herein may be leveraged for other types of imaging procedures. Indeed, any imaging procedures that merge multiple images into a single image may benefit from the described technologies. The technologies may also be utilized for imaging procedures for body structures other than the femurs. Such structures include other bones of the legs, the pelvis, upper and lower bones of the arms, ribcage, and so on.

Figure 1:
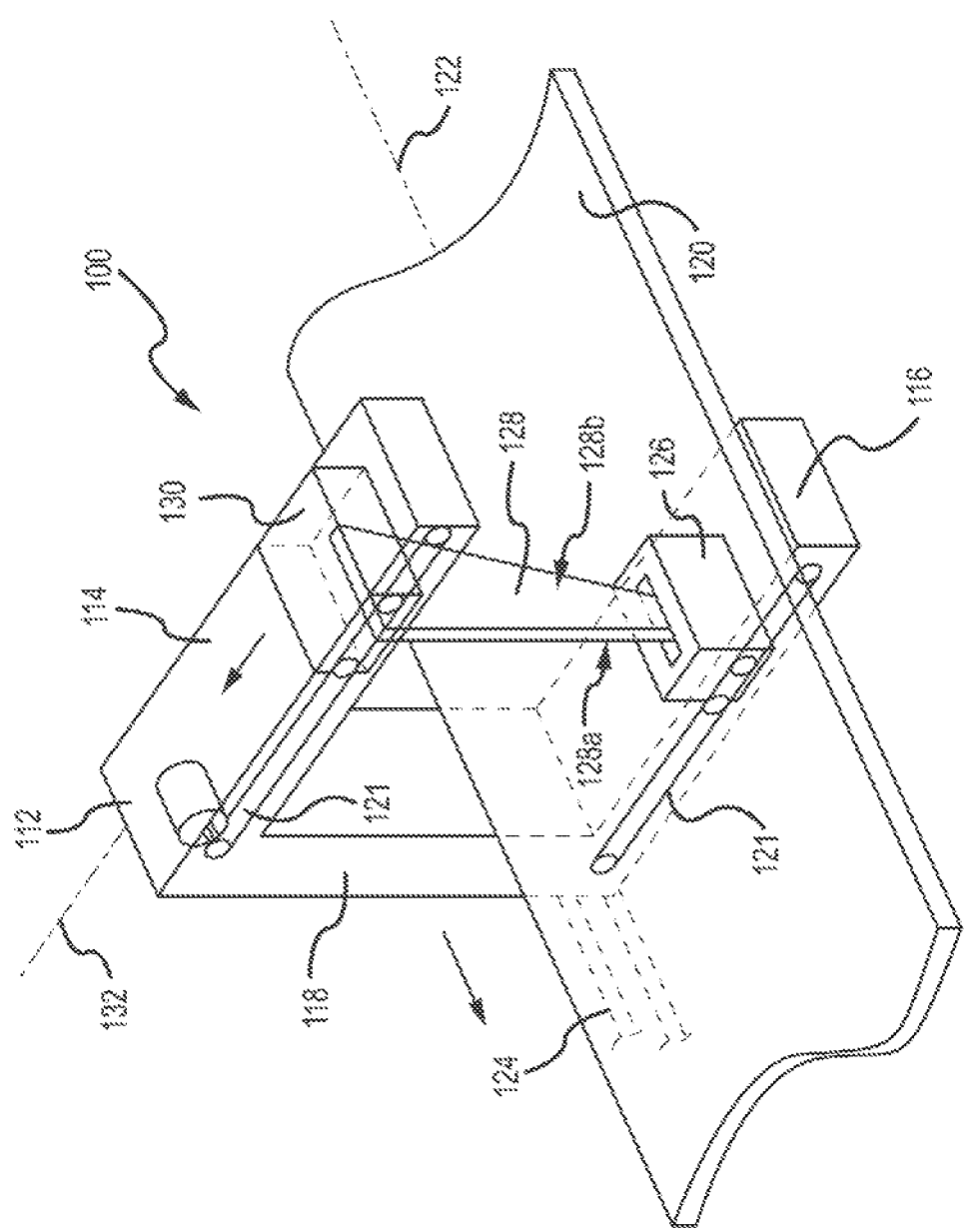
FIG. 1 depicts a perspective view of a transverse scanning densitometer in accordance with one embodiment of the technology.

FIG. 1 depicts a perspective view of a transverse scanning densitometer 100 in accordance with one embodiment of the technology. The densitometer 110 includes a support arm 112 having vertically opposed horizontal arms 114 and 116 separated by vertical bar 118. A horizontal planar patient support table 120 is disposed between the horizontal arms 114, 116 and extends along a longitudinal axis 122. A belt drive system 124 of a type well known in the art, allows motion of the support arm 112 longitudinally along longitudinal axis 122 for the length of the table 120. In other embodiments, other types of drive systems, including racks and gears, may be utilized. The longitudinal axis 122 of the table 120 is generally substantially parallel to a longitudinal axis of a patient lying on the table 120.

An x-ray source 126 is within the lower arm 116. The x-ray source emits a collimated fan beam 128 of x-rays directed upward through the table 120. The beam 128 is detected or otherwise received by a linear detector 130. The fan beam 128 is oriented so that its narrowest extent 128a is along a transverse axis 132 and its widest extent is along the longitudinal axis 122. The table 120 is generally radiolucent so as to provide a support surface without significantly affecting the attenuation of the fan beam 128.

The x-ray source 126 and linear detector 130 may be moved transversely along the transverse axis 132. The x-ray source 126 and linear detector 130 are configured so as to move along the arms 114 and 116. This movement allows for transverse scans of the patient on the table 120. Motion of the x-ray source 126 and detector 130 is synchronized by belt-drive actuation mechanisms 121 as will be well understood to those of ordinary skill in the art. As with the belt drive system 124 described above, other types of drive mechanisms can be utilized in place of the belt-drive actuation mechanisms 124.

Figure 2:
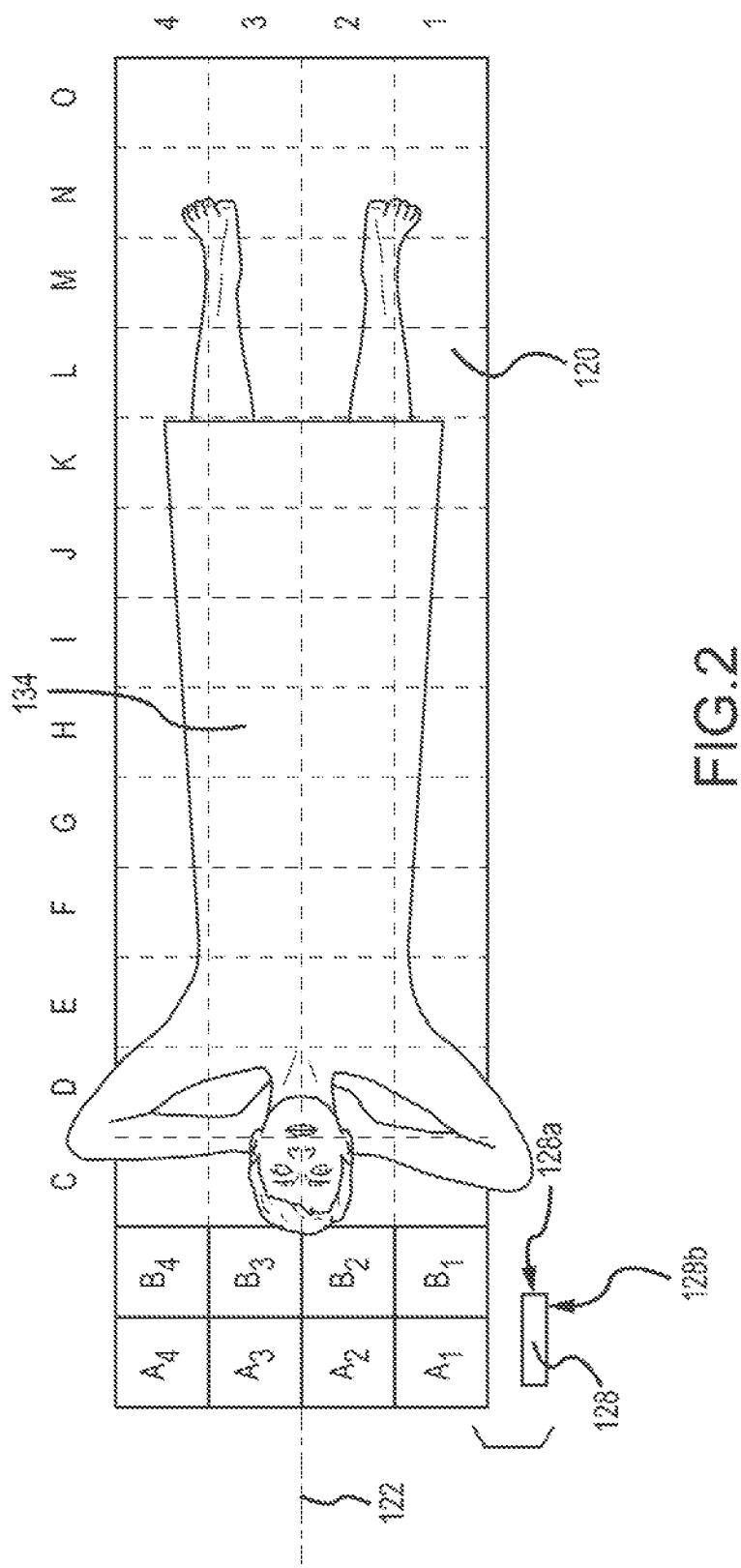
FIG. 2 depicts a top plan view of the table of the transverse scanning densitometer of FIG. 1.

FIG. 2 depicts a top plan view of the table 120 of the transverse scanning densitometer of FIG. 1. Certain of the components described above are not depicted in FIG. 2 for clarity. The fan beam 128 may be scanned over the surface of table 120 and hence may scan the whole body of patient 134 so as to generate a series of transversely extending scan images that may be merged into a single composite image or data set. Alternatively, a plurality of scan images can be merged into a single composite image for a particular body structure or part. For example, a first scan image may encompass, in sequence, areas A1, A2, A3, and A4. The x-ray source and linear detector, described above, may move transversely as required, emitting and receiving x-ray energy along the various sequential areas. At the end of this scan, motion of the support arm, described above, in the longitudinal direction may be performed. For example, the support arm may move towards the feet of the patient, so as to align with a second area of the patient such that the detector may perform a second scan image. The second scan image may be in order of areas B4, B3, B2, and B1. Alternatively, the arm may return to the side of the table 120 where it began the first image scan and scan areas B1, B2, B3, and B4. Because the transverse width of the patient 134 is substantially less than the superior to inferior height of the patient, each scan image, e.g., all of areas 1-4 in each of path A or path B, is acquired at a time closely proximate to its adjacent scan images and thus the risk of patient motion and the amount of patient motion may be substantially reduced. This is one of several marked advantages over imaging systems that that perform scans along the longitudinal axis of the patient.

In other embodiments, transverse scans of particular body parts may be performed. In one example, a complete transverse scan of the ribcage may include scans along scan paths E, F, G, and H. A transverse scan of a single body part that does not extend across an entire transverse scan path can also be performed. For example, the left femur may be scanned by imaging areas I1, I2, J2, J1, K1, and K2. Other transverse scan paths are contemplated.

The radiation source 126 may be a radioisotope or an x-ray tube running at constant voltage to produce a polyenergetic radiation beam. The beam may be subsequently filtered with a K-edge filter to form two energy modes. Alternatively, the radiation source 126 may be an x-ray tube run in a switched voltage mode where the voltage on the x-ray tube is periodically changed from a high to low voltage shifting the energy spectrum of the produced x-ray beam. Data is acquired by a broad band detector 130 and is sequentially high and low energy data as may be used in dual energy measurements. Other techniques including rotating filter wheels and the like may be used to produce sequential dual energy beams.

Figure 3:
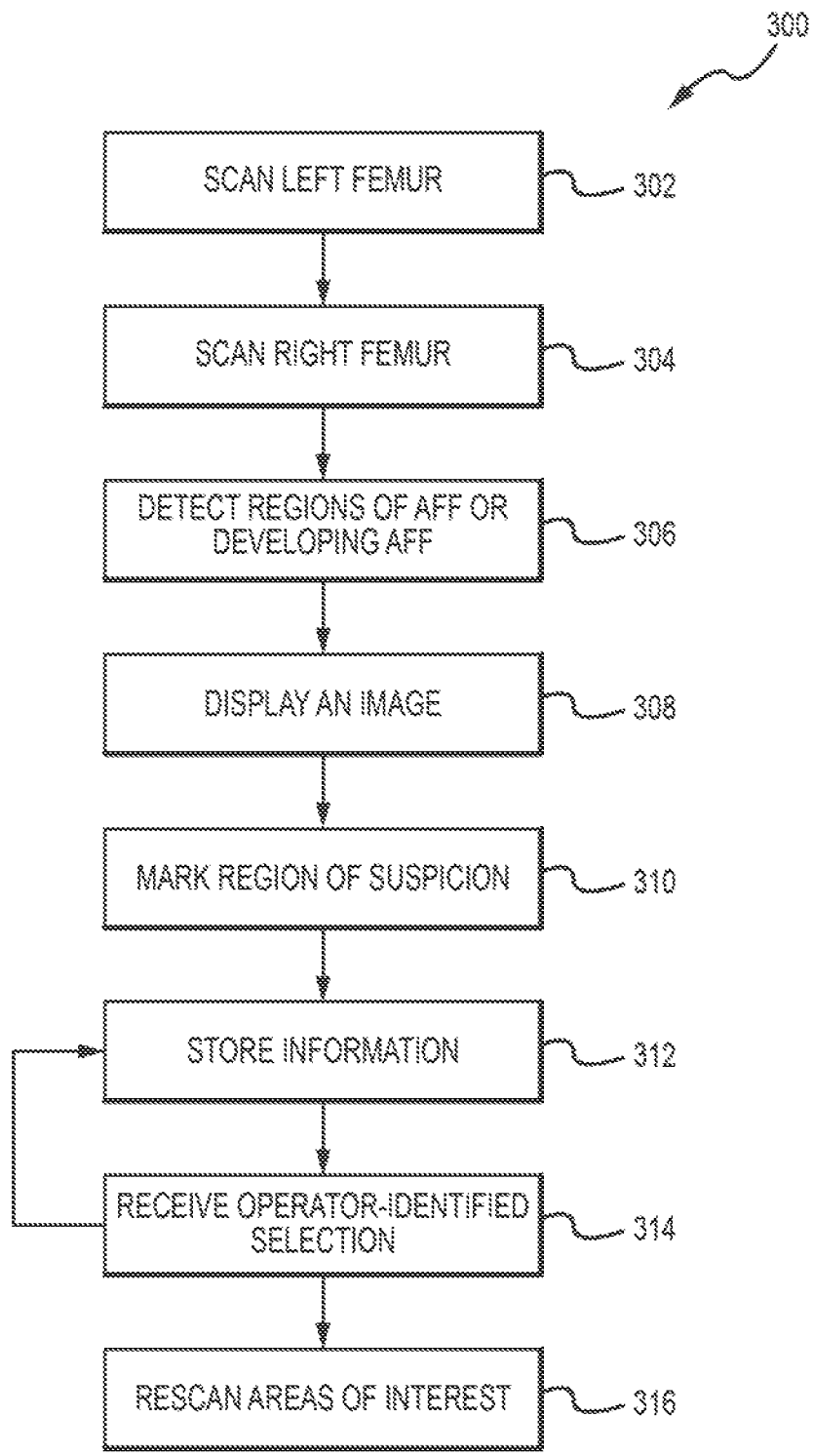
FIG. 3 depicts a method of performing a transverse scanning procedure in accordance with one embodiment of the technology.

FIG. 3 depicts a method 300 of performing a transverse scanning procedure in accordance with one embodiment of the technology. The method 300 is utilized to detect AFFs with a bone densitometer and utilizes a transverse, small angle fan beam. The small angle fan beam may significantly reduce parallax and height dependency problems when adjacent images are merged together. Further, the images for each scan may be merged together with different amounts of overlap, as determined by an analysis of the image itself, for example, using a correlation between adjacent bone structures in different scan images. This correlation reveals the height of the image structure allowing for correction of magnification. Correction of magnification provides for more accurate quantitative measurement of quantities that are magnification dependent, such as bone density.

Figure 4:
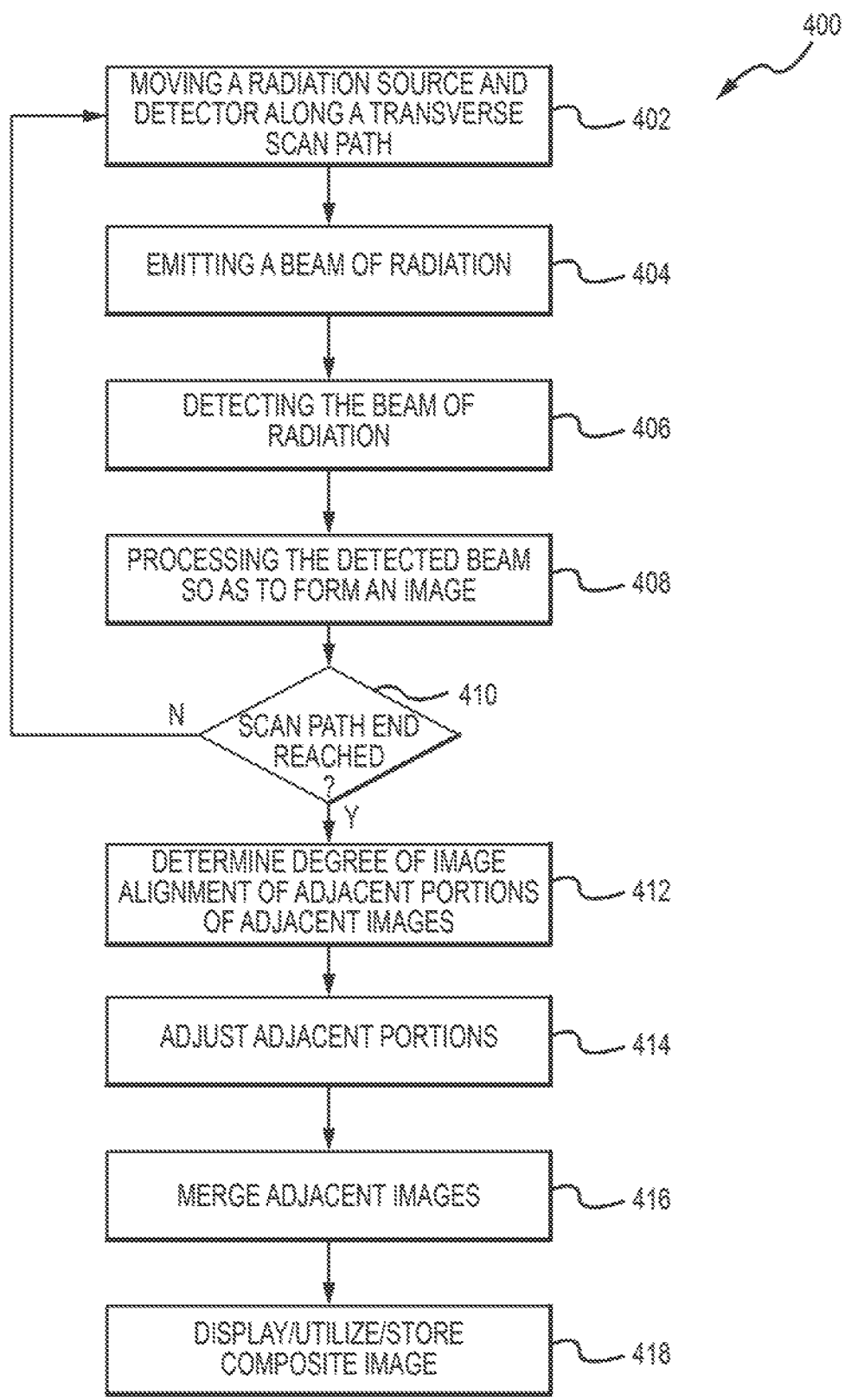
FIG. 4 depicts a method of generating images during a transverse scanning procedure in accordance with an embodiment of the technology.

The method begins at operation 302, where the bone densitometer scans a first portion of the left femur. In operation 304, a corresponding first portion of the right femur is scanned. Both operations 302 and 304 are performed in a single transverse scan (e.g., in one non-limiting example from the supracondylar flare to the head of the femur or the lesser trochanter) allowing BMD of both hips to be measured and, optionally, as well as both femurs to be visualized for the detection of AFF. AFF is often bilateral (e.g., presenting in both right and leg femurs), so scanning transversely across both femurs may be advantageous to the detection and assessment of AFFs. Detection of regions of AFF or developing AFF occurs at operation 306. The region of the AFF or developing AFF may be monitored by measuring the BMD of the region using subregions extending over the AFF region which could be matched with serial scans from the bone densitometer. Operation 306 also contemplates automatic detection of AFF or developing AFF by utilizing image recognition software to identify faint focal reaction, early callus formation, either periosteally or endosteally to the lateral cortex, and/or by detection a localized "bump" or "thickening" in the lateral cortex. The image generated during the scan can then be displayed, operation 308, on an associated computer or display screen. FIG. 4, below, describes methods of generating images from transverse scans.

A region of suspicion or interest, as determined by the software in operation 306, for example, may be highlighted to the operator by marking the displayed image 310. Information (e.g., coordinates) about the location of AFF or regions of suspicion or interest may be stored with the image, operation 312. In certain embodiments, the operator could optionally mark and/or indicate a section of the femur that may appear suspicious and/or that may benefit from another scan (e.g., one at a higher resolution). Marking may be performed by the operator circling an area of interest on a touch-screen display. This selection is received by the system, operation 314, and stored as additional information in operation 312. This process may continue until the operator concludes her selections of areas of interest. Once all areas of interest are identified, rescanning may be performed at operation 316. Rescanning may utilize a slower scan speed and/or may be centered in the narrow fan beam to avoid overlap or stitching artifacts. Additionally or alternatively, more tube current and/or a different collimator may be utilized to narrow the beam and increase the resolution. The scan of the femurs described in method 300 could also be utilized for the typical proximal femur BMD assessment.

FIG. 4 depicts a method 400 of generating images during a transverse scanning procedure in accordance with an embodiment of the technology. The method 400 provides for a scanning bone densitometer having a radiation source collimated to produce or emit a beam of radiation directed across a patient to an electronic radiation detector, the latter of which receives, detects, or otherwise measures the beam of radiation passing through the patient. A scanning assembly moves the radiation source and radiation detector along at least one scan path transverse to a longitudinal axis of a patient, operation 402. While moving, the radiation source emits the beam of radiation, operation 404, which is detected by the radiation detector, operation 406. The detected beam is then processed so as to form an image, operation 408. Since the beam has a predefined width, the size of each image is based on the beam width and a length of travel of the scanning assembly. Any number of discrete images may be formed as the scanning assembly travels along the transverse scan path. As the scanning assembly traverses the scan path, one or more sensors determine a position thereof. If the end of the scan path is not reached as depicted in operation 410, flow branches to NO and movement of the scanning assembly (as well as operations 402-408) continue, thus generating a plurality of images along the scan path. Once the end of the scan path is reached at operation 410, flow branches YES, where a degree of image alignment is then determined at operation 412.

In certain embodiments, the image alignment of adjacent portions of adjacent images is determined. The size of the adjacent portions may be determined based on, e.g., number of pixels in the image, a percentage of the total area of the image, or other factors. These adjacent portions of the adjacent images may be adjusted, operation 414, so as to allow different degrees of overlap to better match structures within the images having various heights within the patient. The degree of image alignment may evaluate only the bone portion of the image. The method 400 may improve the ability to match the images by eliminating structure such as soft tissue whose matching is not critical. In other embodiments, determining the degree of image alignment may include determining a structure height based on a known divergence of the radiation beams and the determined overlap, thus improving image alignment. The height may be used to scale each scan image prior to merging adjacent scan images. Thus, the system and method described herein may employ the difference in overlap between adjacent scan images to correct the magnification of the image. Thereafter, the adjacent images are merged at overlapping areas, operation 416, to form a composite image that includes all of the combined adjacent images. Prior to merging, the images may be weighted so as to eliminate any disproportionate influence of redundant data in the images. Regardless, the proposed technologies do not rely on weighting alone, as such methods may produce a blurring of the merged image. Blurring of the image may be reduced or eliminated by correcting overlap of the images, as described herein. This composite image has an overlap corresponding to a best matching of the plurality of scan images. In operation 418, the composite image may then be stored, displayed, and/or otherwise utilized for marking, as described above in FIG. 3.

The patient support may support a supine patient with the patient's head and feet lying along a longitudinal axis and the scanning assembly may move the radiation source and electronic detector along a series of transverse scan paths substantially perpendicular to the longitudinal axis across the patient to acquire the scan images. Such a method includes operations similar those depicted in FIG. 4. As the end of a scan path is reached, the system may then traverse a second transverse scan path that is substantially parallel to the first transverse scan path. Images obtained along the second transverse scanned path are processed as described in FIG. 4, operations 412-416. However, degree of image alignment may be determined for both of adjacent images in the same scan path, as well as adjacent images in adjacent scan paths. Such processing can produce a master composite image that includes all images in all scan paths, which may then be utilized as described above in FIG. 3.

Figure 5:
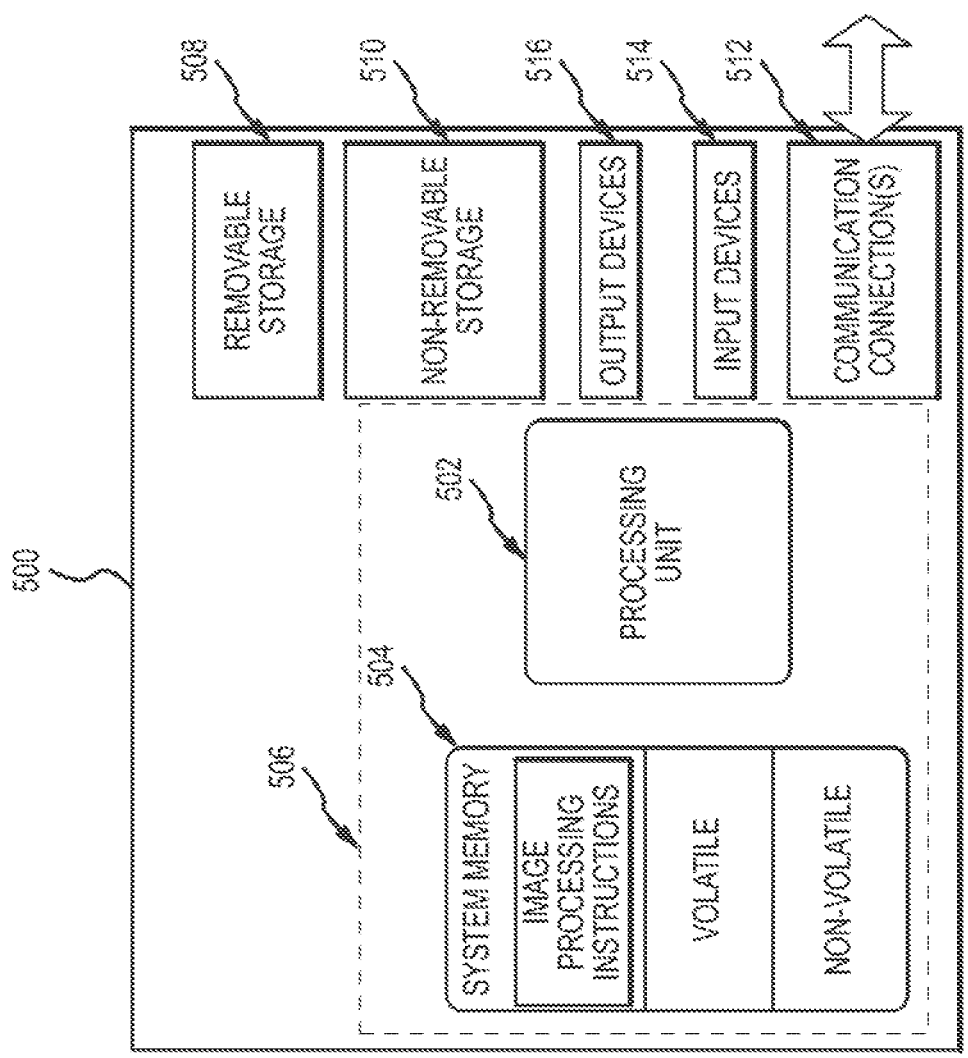
FIG. 5 illustrates one example of a suitable operating environment in which one or more of the present examples can be implemented.

FIG. 5 illustrates one example of a suitable operating environment 500 in which one or more of the present embodiments can be implemented. This operating environment may be incorporated directly into a scanning system, or may be incorporated into a computer system discrete from, but used to control, a scanning system such as described herein. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 500 typically includes at least one processing unit 502 and memory 504. Depending on the exact configuration and type of computing device, memory 504 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 5 by dashed line 506. Further, environment 500 can also include storage devices (removable, 508, and/or non-removable, 510) including, but not limited to, magnetic or optical disks or tape. Similarly, environment 500 can also have input device(s) 514 such as touch screens, keyboard, mouse, pen, voice input, etc., and/or output device(s) 516 such as a display, speakers, printer, etc. Also included in the environment can be one or more communication connections 512, such as LAN, WAN, point to point, Bluetooth, RF, etc.

Operating environment 500 typically includes at least some form of computer readable media. Computer readable media can be any available media that can be accessed by processing unit 502 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 500 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 500 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 500 is part of a network that stores data in remote storage media for use by the computer system 500.

Figure 6:
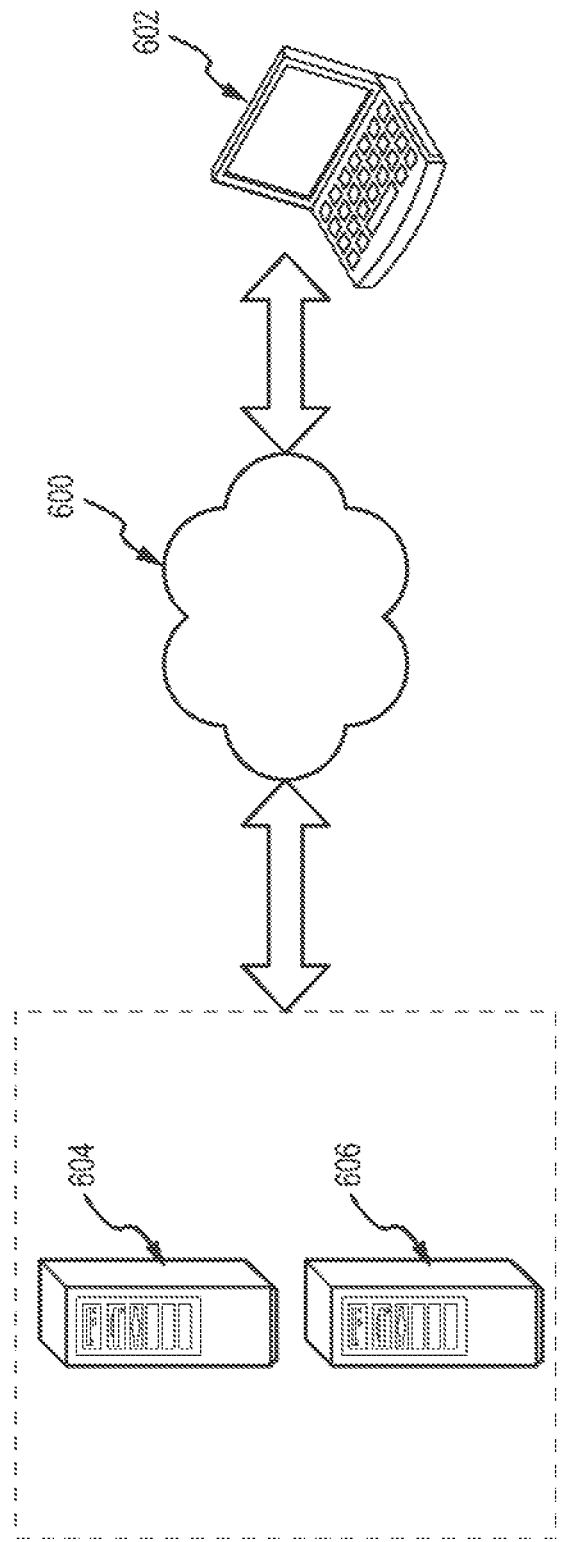
FIG. 6 is an embodiment of a network in which the various systems and methods disclosed herein may operate.

FIG. 6 is an embodiment of a network 600 in which the various systems and methods disclosed herein may operate. In embodiments, a client device, such as client device 602, may communicate with one or more servers, such as servers 604 and 606, via a network 608. In embodiments, a client device may be a laptop, a personal computer, a smart phone, a PDA, a netbook, or any other type of computing device, such as the computing device in FIG. 5. In embodiments, servers 604 and 606 may be any type of computing device, such as the computing device illustrated in FIG. 5. Network 608 may be any type of network capable of facilitating communications between the client device and one or more servers 604 and 606. Examples of such networks include, but are not limited to, LANs, WANs, cellular networks, and/or the Internet.

In embodiments, the various systems and methods disclosed herein may be performed by one or more server devices. For example, in one embodiment, a single server, such as server 604 may be employed to perform the systems and methods disclosed herein, such as the method for scanning and image processing. Client device 602 may interact with server 604 via network 608. In further embodiments, the client device 602 may also perform functionality disclosed herein, such as scanning and image processing, which can then be provided to servers 604 and/or 606.

In alternate embodiments, the methods and systems disclosed herein may be performed using a distributed computing network, or a cloud network. In such embodiments, the methods and systems disclosed herein may be performed by two or more servers, such as servers 604 and 606. Although a particular network embodiment is disclosed herein, one of skill in the art will appreciate that the systems and methods disclosed herein may be performed using other types of networks and/or network configurations.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. A method of scanning a patient, the method comprising:
   moving a radiation source and a radiation detector along a first scan path substantially transverse to a longitudinal axis of the patient, wherein the first scan path is across a first femur from a supracondylar flare to a head of the first femur and across a second femur from a supracondylar flare to a head of the second femur;
   emitting a first beam of radiation from the radiation source during movement along the first scan path;
   detecting the first beam of radiation at the radiation detector during movement along the first scan path;
   processing the detected beam so as to form a first image of a first area of the patient along the scan path, wherein the first area includes both the first femur and the second femur;
   identifying a region in the first image;
   moving the radiation source and the radiation detector along a region scan path corresponding to the identified region;
   emitting a region beam of radiation from the radiation source during movement along the region scan path; and
   detecting the region beam of radiation at the radiation detector during movement along the region scan path.

2. The method of claim 1, further comprising processing the detected first beam so as to form a second image of a second area of the patient along the first scan path, wherein the second area of the patient is adjacent to the first area.

3. The method of claim 2, further comprising determining a degree of image alignment between adjacent portions of the first image and the second image.

4. The method of claim 3, wherein determining the degree of image alignment comprises analyzing only a selected structure of the patient.

5. The method of claim 4, wherein the selected structure comprises a bone.

6. The method of claim 4, wherein determining the degree of image alignment comprises determining a height of the selected structure.

7. The method of claim 6, further comprising scaling at least one of the first image and the second image based at least in part on the height of the selected structure.

8. The method of claim 1, wherein the first scan path encompasses a plurality of adjacent areas of the patient disposed along the first scan path.

9. The method of claim 1, wherein the identification is performed manually.

10. The method of claim 1, wherein the identification is performed automatically.

11. The method of claim 1, Wherein the region corresponds to a location of a potential atypical femoral fracture.

12. The method of claim 1, wherein moving the radiation source and the radiation detector along the first scan path comprises moving the radiation source and the radiation detector transversely across a portion of the first femur prior to moving the radiation source and the radiation detector transversely across a portion of the second femur.

13. A method comprising:
   measuring a bone mass density of two hips of a patient based at least in part on a hip scan beam;
   emitting a first beam of radiation along a first scan path, wherein the first scan path encompasses at least a portion of a length of a femur of the patient;
   detecting the first beam of radiation along the first scan path;
   processing the detected first beam so as to fonn a plurality of first scan path images of the patient;

determining a degree of image alignment between adjacent portions of adjacent images of the plurality of first scan path images;

merging the adjacent images of the first scan path images at the adjacent portions to form a first scan path composite image; and identifying a region in the first scan path composite image, wherein the region is associated with at least one of an atypical femoral fracture and a developing atypical femoral fracture.

14. The method of claim 13, further comprising:

emitting a second beam of radiation along a second scan path, wherein the second scan path is substantially parallel to the first scan path;

detecting the second beam of radiation along the second scan path;

processing the detected second beam so as to form a plurality of second scan path images of the patient;

determining a degree of image alignment between adjacent portions of adjacent images of the plurality of second scan path images; and determining a degree of image alignment between adjacent portions of adjacent images of the plurality of second scan path images and the plurality of first scan path images.

15. The method of claim 14, further comprising merging the adjacent images of the second scan path images at the adjacent portions to form a second scan path composite image.

16. The method of claim 14, further comprising merging the adjacent images of the second scan path images and the first scan path images at adjacent portions to form a master composite image.

17. The method of claim 13, wherein determining the degree of image alignment comprises analyzing only a selected structure of the patient.

18. The method of claim 17, wherein the selected structure comprises a bone.

19. The method of claim 17, wherein determining the degree of image alignment comprises determining a height of the selected structure.

20. The method of claim 19, further comprising scaling at least one of a plurality of adjacent first scan path images based at least in part on the height of the selected structure.

21. The method of claim 13, further comprising emitting a region beam of radiation from a radiation source, wherein the region beam of radiation is different than the first beam of radiation.

\* \* \* \* \*